United States Patent
Hisanaka et al.

(10) Patent No.: US 6,517,925 B1
(45) Date of Patent: *Feb. 11, 2003

(54) LIQUID-PERVIOUS TOPSHEET FOR DISPOSABLE ABSORBENT ARTICLE AND PROCESS FOR MAKING THE SAME

(75) Inventors: Takayuki Hisanaka, Kagawa-ken (JP); Hisashi Takai, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 120 days.

This patent is subject to a terminal disclaimer.

(21) Appl. No.: 09/587,121

(22) Filed: Jun. 2, 2000

(30) Foreign Application Priority Data

Jun. 3, 1999 (JP) .......................................... 11-157016

(51) Int. Cl.[7] .............................................. A61F 13/15
(52) U.S. Cl. ...................... 428/138; 428/131; 428/133; 428/137; 604/358; 604/365; 604/378; 604/383; 604/385.01; 604/385.101
(58) Field of Search ................................ 428/131, 133, 428/137, 138; 604/358, 365, 366, 378, 383, 385.01, 385.08, 385.101, 385.31

(56) References Cited

U.S. PATENT DOCUMENTS

| | | | | |
|---|---|---|---|---|
| 4,282,874 A | * | 8/1981 | Mesek | 604/365 |
| 4,629,643 A | | 12/1986 | Curro et al. | 428/156 |
| 6,117,524 A | * | 9/2000 | Hisanaka et al. | 428/131 |

FOREIGN PATENT DOCUMENTS

| | | |
|---|---|---|
| DE | 44 37 165 A1 | 4/1996 |
| EP | 0 919 212 A2 | 6/1999 |
| JP | 7-328001 | 12/1995 |

* cited by examiner

Primary Examiner—Harold Pyon
Assistant Examiner—Alicia Chevalier
(74) Attorney, Agent, or Firm—Baker & Daniels

(57) ABSTRACT

A topsheet for a disposable absorbent article that includes a first plastic film layer, a second plastic film layer and a fibrous assembly layer disposed between these two layers. The first plastic film layer includes a plurality of first plane regions spaced apart from one another that extend parallel to one another in one direction and the second plastic film layer includes a plurality of second plane regions spaced apart from one another that extend parallel to one another in the one direction. Of the first and second plane regions, at least the first plane regions are formed with bridge-like regions and first rising regions.

6 Claims, 9 Drawing Sheets

LIQUID-PERVIOUS TOPSHEET FOR DISPOSABLE ABSORBENT ARTICLE AND PROCESS FOR MAKING THE SAME

BACKGROUND OF THE INVENTION

This invention relates to a liquid-pervious topsheet for disposable absorbent articles such as disposable diapers and menstruation pads and a process for making the same.

Japanese Patent Application Disclosure No. 1995-328061 describes a liquid-pervious topsheet used in a disposable body fluids absorbent article, particularly, a menstruation pad comprising a nonwoven fabric and a liquid-impervious thermoplastic film. The plastic film is provided in the form of a plurality of film strips extending parallel one to another at predetermined intervals and bonded to the upper surface of the nonwoven fabric. The nonwoven fabric is formed with high density regions covered with the plastic film and with low density regions exposed between each pair of adjacent film strips. With such a topsheet, menstrual fluids discharged on the upper surface of the topsheet permeate the low density regions exposed between each pair of adjacent film strips into a core underlying the topsheet. The core has its upper side entirely covered with the nonwoven fabric and partially covered with the film strips so that the core soiled with menstrual fluids is not visually inconspicuous. An amount of menstrual fluids once discharged on the low density region tends to transfer to the high density regions and, as a result, the high density regions contain a relatively large amount of menstrual fluids. In spite of the large amount of menstrual fluids possibly contained in the high density regions, soil due to this is inconspicuous since the high density regions directly underlie the respective film strips. This known topsheet is claimed to alleviate a visual discomfort possibly experienced by a wearer of the article when the user disposes of the used article.

However, one of the problems associated with the forsaid conventional topsheet used in the menstruation pad is that, in the low density regions exposed between each pair of adjacent film strips, the portions of the core underlying the low density regions and soiled with menstrual fluids can be seen through the nonwoven fabric making the part of the topsheet.

Another problem associated with the foresaid conventional topsheet is that, if the topsheet rubs a wearer's skin transversely of the direction in which the film strips extend as the wearer s body moves, edges of the respective film strips may irritate the wearer's skin as knife edges.

SUMMARY OF THE INVENTION

It is an object of this invention to provide a topsheet for a body fluids absorbent article that allows a soiled with body fluids to be concealed over a large range and simultaneously provides a smooth and velvet touch.

The object set forth above is achieved by a first aspect of this invention relating to a liquid-pervious topsheet used in body fluids absorbent article, and by second to fourth aspects of this invention relating to a process for making such a liquid-pervious topsheet.

According to the first aspect of this invention, there is provided liquid-pervious topsheet for a body fluids absorbent article comprising a first plastic film layer forming an upper surface of the topsheet, a second plastic film layer forming a lower surface of the topsheet and a fibrous assembly layer disposed between the first and second plastic film layers and bonded to the first and second plastic film layers, wherein:

the first plastic film layer includes a plurality of first plane regions spaced one from another and extending in parallel one to another in one direction and the second plastic film layer includes a plurality of second plane regions spaced one from another and extending in parallel one to another in the one direction wherein each of the first and second plane regions has a thickness of 0.001~0.05 mm and a width of 0.03~1 mm and wherein, of each pair of the first plane regions adjacent to each other and each pair of the second plane regions adjacent to each other, at least each pair of the first plane regions adjacent to each other are connected with each other by a plurality of bridge-like regions extending between the plane regions adjacent to each other;

of the first and second plane regions, at least the first plane regions are formed along edges thereof with first rising regions extending upward from an upper surface of the first plane regions in an irregular array of substantially triangular tooth;

the second plastic film layer partially underlies regions of the fibrous assembly layer defined between a lower surface of each pair of the first plane regions adjacent to each other; and the fibrous assembly layer is bonded between the first plane regions and an upper surface of the second plane regions, and contains of hydrophilic fiber of 5 wt % or higher.

According to the second aspect of this invention, there is provided a process for making a liquid-pervious topsheet for a body fluids absorbent article comprising the steps of:

a. continuously feeding a composite web comprising a plastic film and a fibrous assembly underlying the plastic film and bonded to a lower surface of the plastic film in one direction;

b. subjecting a lower surface of the continuously fed composite web to high pressure columnar water streams ejected from a plurality of nozzles arranged transversely of the web and thereby rupturing the plastic film by the high pressure columnar water streams in the one direction according to traces of the high pressure columnar water streams to form the plastic film with a plurality of first plane regions extending in parallel one to another in the one direction, a plurality of openings extending in parallel one to another in the one direction between each pair of the first plane regions adjacent to each other, a plurality of first rising regions extending from edges of the first plane regions defining the openings substantially in the same direction as the high pressure columnar water streams, in an irregular array of substantially triangular tooth, and a plurality of bridge-like regions extending across each of the openings to connect each pair of the first plane regions adjacent to each other; and c. bonding a plurality of plastic film strips extending in parallel one to another in the one direction to a lower surface of the fibrous assembly so that the plastic film strips at least partially underlie portions of the fibrous assembly defined by each of the openings.

According the third aspect of this invention, there is provided a process for making a liquid-pervious topsheet for a body fluids absorbent article comprising the steps of:

a. continuously feeding a composite web comprising a plastic film and a fibrous assembly underlying the plastic film and bonded to a lower surface of the plastic film in one direction;

b. subjecting an upper surface of the continuously fed composite web to high pressure columnar water streams ejected from a plurality of nozzles arranged transversely of the web and thereby rupturing the plastic film by the high pressure columnar water streams in the one direction according to traces of the high pressure columnar water streams;

c. subjecting a lower surface of the composite web, substantially in accordance with the traces of the high pressure columnar water streams, to high pressure columnar water streams to form the plastic film with a plurality of first plane regions extending in parallel one to another in the one direction, a plurality of openings extending in parallel one to another in the one direction between each pair of the first plane regions adjacent to each other, a plurality of first rising regions extending from edges of the first plane regions defining the openings substantially in the same direction as the high pressure columnar water streams in an irregular array of substantially triangular tooth, and a plurality of bridge-like regions extending across each of the openings to connect each pair of the plane regions adjacent to each other; and d. bonding a plurality of plastic film strips extending in parallel one to another in the one direction to a lower surface of the fibrous assembly so that the plastic film strips at least partially underlie portions of the fibrous assembly defined by each of the openings.

According to the fourth aspect of this invention, there is provided a process for making a liquid-pervious topsheet for a body fluids absorbent article comprising the steps of:

a. continuously feeding a composite web in one direction, the composite web comprising an upper plastic film, a lower plastic film and a fibrous assembly disposed between the upper and lower plastic films and bonded to a lower surface of the upper plastic film and to an upper surface of the lower plastic film in one direction; and b. subjecting an upper surface of the continuously fed composite web to high pressure columnar water streams ejected from a plurality of nozzles arranged transversely of the web and thereby rupturing the upper and lower plastic films in according with traces of the high pressure columnar water streams in the one direction to form the upper and lower plastic films with a plurality of first plane regions extending in parallel one to another in the one direction, a plurality of openings extending in parallel one to another in the one direction between each pair of the first plane regions adjacent to each other, a plurality of first rising regions extending from edges of the first plane regions defining the openings substantially in the same direction as the high pressure columnar water streams in an irregular array of substantially triangular tooth, and a plurality of bridge-like regions extending across each of the openings to connect each pair of the plane regions adjacent to each other.

DETAILED DESCRIPTION OF THE PREFERRED EMBODIMENTS

A liquid-pervious topsheet for body fluids absorbent articles and a process for making the same will be described in more details with reference to the accompanying drawings.

Figure 1:
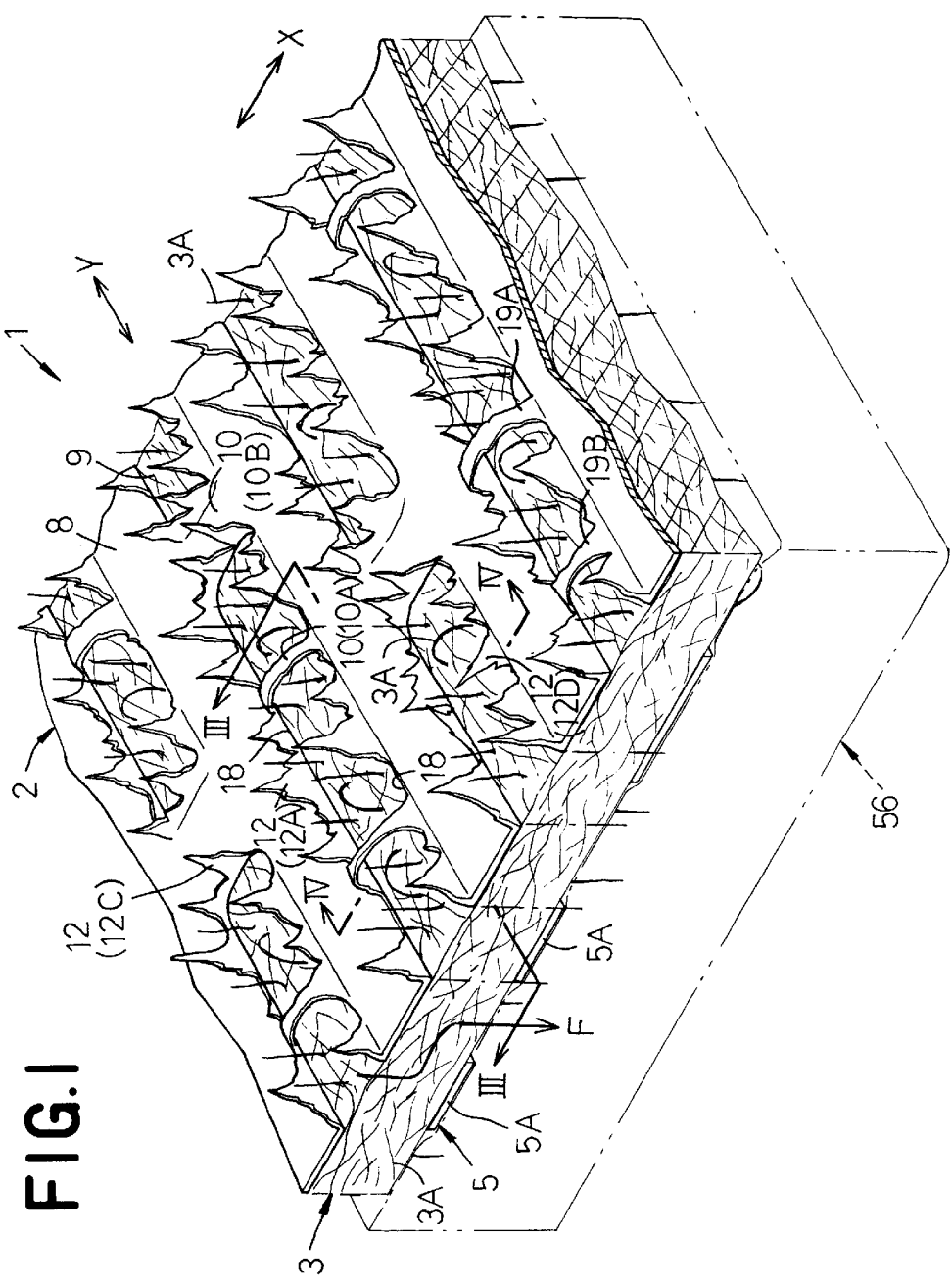
FIG. 1 is a perspective view showing a topsheet according to one embodiment of the present invention.
Figure 2:
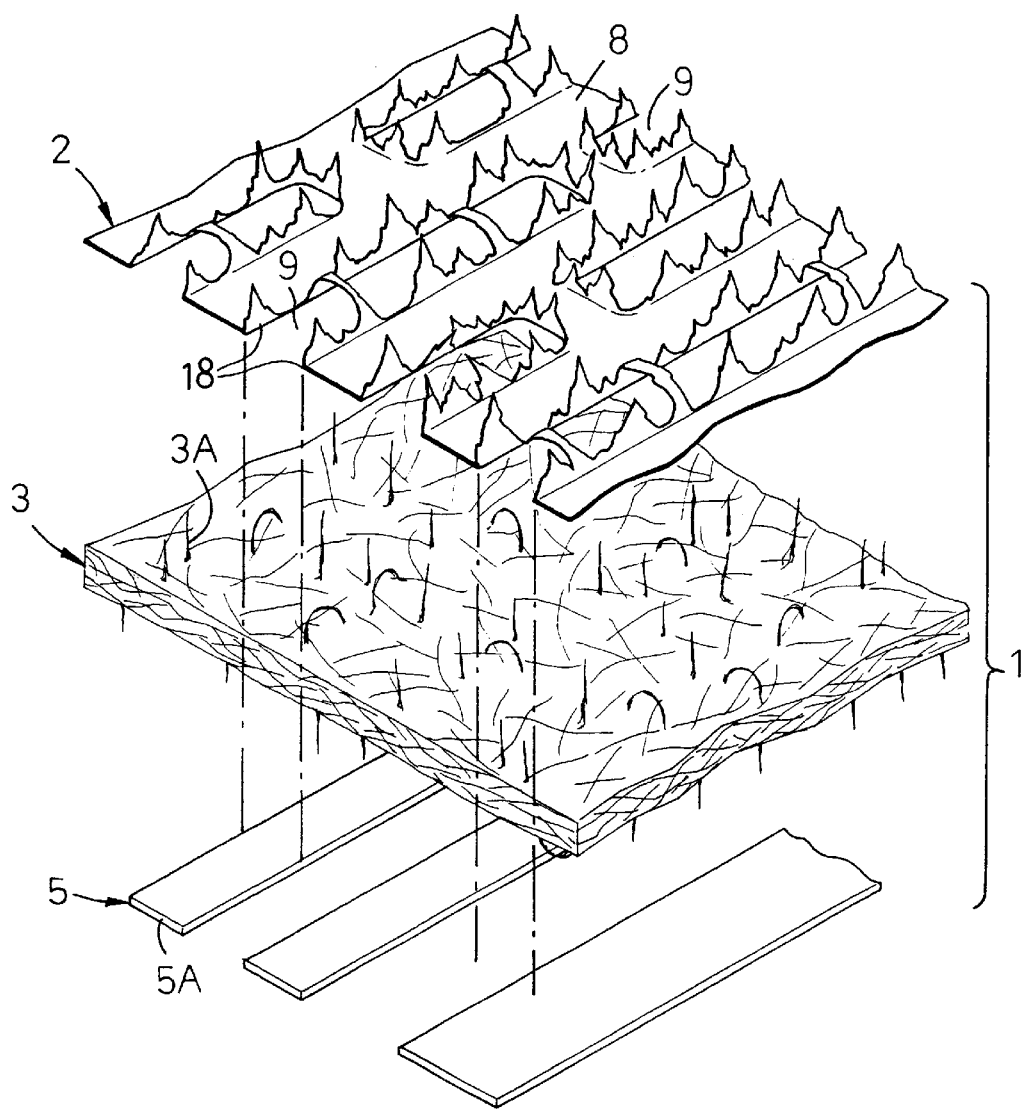
FIG. 2 is an exploded perspective view showing the topsheet.

FIG. 1 is a perspective view showing a liquid-pervious topsheet 1 used in body fluids absorbent articles such as disposable diapers and menstruation pads and FIG. 2 is a perspective view showing the topsheet 1 with its components vertically exploded. The topsheet 1 comprises an upper plastic film layer 2, a lower plastic film layer 5 and a fibrous assembly layer 3 disposed between these two film layers 2, 5.

The upper film layer 2 is flexible and comprises various regions as follows: a plurality of substantially plane regions 8 extending in parallel one to another in a direction as indicated by a double-headed arrow Y; a plurality of openings 9 extending in the direction Y between each pair of adjacent plane regions 8; bridge-like regions 10 extending across each of the openings 9 in a direction as indicated by a double-headed arrow X to connect opposite edges 18 of each of the openings 9; and rising regions 12 extending upward from the edges 18 of the plane regions 8. The rising regions 12 irregularly undulate in the direction Y to form sawtooth waves.

The fibrous assembly layer 3 is flexible and bonded to the lower surface of. the upper film layer 2 in its plane regions 8 so that the upper surface of the fibrous assembly layer 3 may be exposed within the openings 9. Within the openings 9, component fibers 3A of the assembly layer 3 partially extend upward linearly or so as to describe circular arcs.

The lower film layer 5 comprises a plurality of film strips 5A extending in parallel one to another in the direction Y and bonded to the lower surface of the fibrous assembly layer 3. In this manner, the lower film layer 5 forms at least a part of the lower surface of the topsheet 1. The fibrous assembly layer 3 has its lower surface exposed between each pair of adjacent film strips 5A, 5A and, in these exposed regions, component fibers 3A of the assembly layer 3 partially extend downward so as to describe straight lines or circular arcs.

Figure 3:
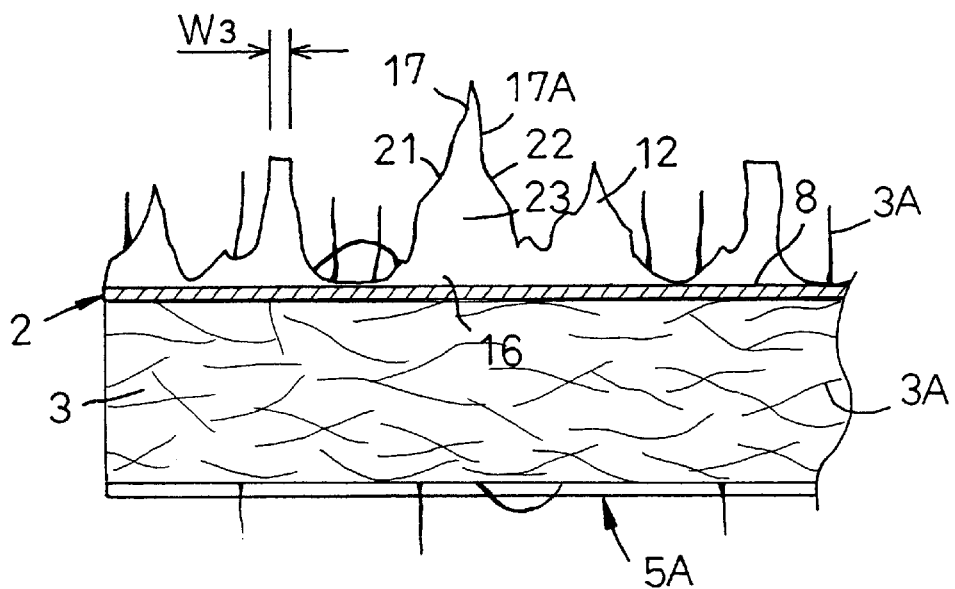
FIG. 3 is a sectional view taken along line III—III in FIG. 1.
Figure 4:
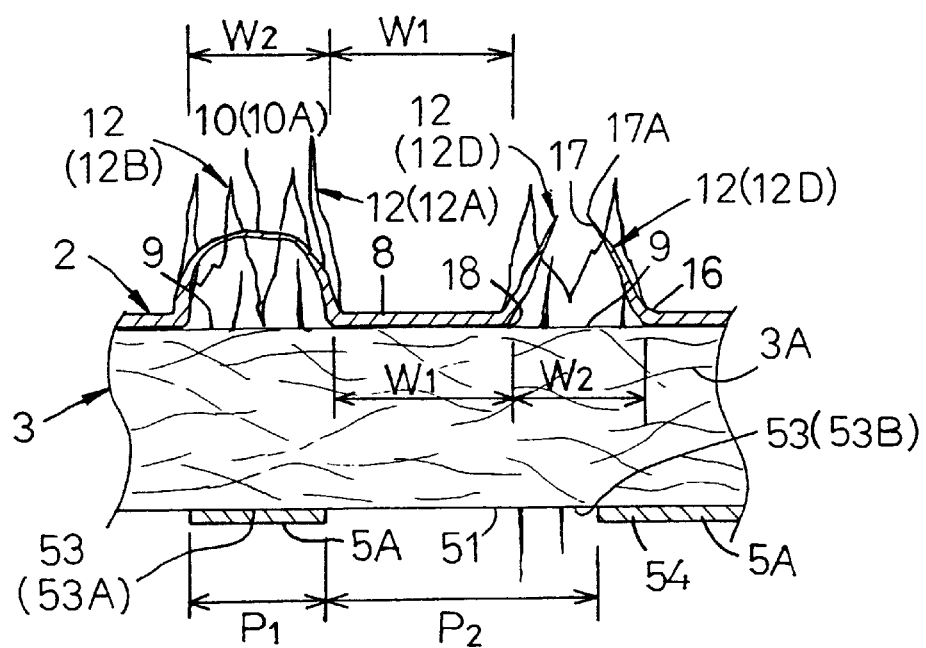
FIG. 4 is a sectional view taken along line IV—IV in FIG. 1.

Referring to FIGS. 1 and 2, single dot chain lines extending downward from the edges 18 of the upper film layer 2 show lines for projecting the respective openings 9 upon the lower surface of the fibrous assembly layer 3. Each of the film strips 5A as a whole or partially underlies each region of the fibrous assembly layer 3 defined by each of the openings 9. FIGS. 3 and 4 are sectional views respectively taken along lines III—III and IV—IV in FIG. 1.

Referring to FIGS. 3 and 4, the upper film layer 2 is made of thermoplastic material, of which the plane regions 8 have a thickness of 0.001~0.05 mm and a width $W_1$ of 0.03~1 mm as measured in the direction X between each pair of adjacent openings 9, 9. Most of the openings 9 has a larger dimension in the direction Y. Each of the openings 9 preferably has a width $W_2$ of 0.05~1 mm and a length corresponding to 1.5 times of the width $W_2$ or larger.

The bridge-like regions 10 of the upper plastic film layer 2 are formed intermittently in the direction Y. The bridge-like regions 10 include arc-shaped bridge-like regions 10A having their proximal ends 19A appearing to extend from the plane regions 8 and arc-shaped bridge-like regions 10A having their proximal ends 19B appearing to extend in continuity with the rising regions 12, and plane bridge-like regions 10B which are frush with the plane regions 8 (Refer also to FIG. 1). The bridge-like regions 10 preferably have a thickness equal to or less than the thickness of the plane regions 8 and a width $W_3$ in the direction Y (Refer to FIG. 3) of at least 0.001~2 mm.

A large majority 12A of the rising regions 12 are formed by a portion of the upper plastic film layer 2 extending upward from edges of the film layer 2. The rising regions 12A have proximal ends 16 contiguous to the respective plane regions 8 and free ends 17 extending upward from the proximal ends 16. The upper edges 17A of the respective free ends 17 undulate along the respective edges 18. A height of the upper edges 17A as measured from the plane regions 8 varies in a range of 0~1 mm. The rising regions 12 include those 12C formed along edges of the bridge-like regions 10 and having substantially the same height as the rising regions 12A (Refer also to FIG. 1).

The embodiment in which the upper edges 17A of the rising regions 12A undulate to form sawtooth-like portions will be described in more details with reference to FIG. 3. The rising regions 12A comprise an irregular array of substantially triangular sawtooth-like edges 23 each defined by a substantially rightward ascendant oblique side 21, a substantially leftward ascendant oblique side 22 and the proximal end 16 extending between these two oblique sides 21, 22. The rising regions 12C also may undulate in the similar manner to the rising regions 12A. The rising regions 12 comprising the rising regions 12A, 12C have a thickness equal to or less than the thickness of the plane regions 8 so that the rising regions 12 may be smoothly deformed as they come in contact with a wearer's skin and consequently the topsheet 1 may give the wearer a smooth and soft velvet touch. While it will be difficult to visually recognize the individual rising regions 12, a plurality of rising regions 12 as a whole give the upper surface of the topsheet 1 a fluffy appearance. The rising regions 12 diffusively reflect the light incident thereupon and thereby alleviate surface gloss peculiar to the plastic film.

The upper plastic film layer 2 including a plurality of openings 9 preferably has a breathability of 5~700 cm$^3$/cm$^2$ sec as measured according to the prescription of JIS (Japanese Industrial Standards)-L-1096 and a moisture resistance of 0~200 mm as measured according to the prescription of JIS-L-1092. The film layer 2 is made of material selected from a group consisting of a hydrophobic thermoplastic films, hydrophobic thermoplastic films treated to become hydrophilic and originally hydrophilic plastic films. The film used as stock material for the layer 2 may contain suitable colorant such as titanic oxide or barium sulfate.

The fibrous assembly layer 3 is made of material selected from a group consisting of thermoplastic synthetic fibers, chemical fibers such as rayon fibers, a mixture of these synthetic fibers and chemical fibers, and such synthetic fibers and/or chemical fibers mixed with cotton fibers and/or pulp fibers. The fibrous assembly layer 3 contains hydrophilic fibers of 5 wt % or higher, preferably of 10 wt % or higher, more preferably of 20 wt % or higher. More preferably, the assembly layer 3 comprises a nonwoven fabric having a basis weight of 2~50 g/m$^2$, in which the component fibers are mechanically entangled and heat-sealed or adhesively bonded together. The nonwoven fabric containing thermoplastic synthetic fiber or chemical fiber having a fineness of 0.05~15 deniers may be selected from a group consisting of a spun bond nonwoven fabric, a point bond nonwoven fabric, a thermal bond nonwoven fabric such as an air-through nonwoven fabric, a melt blown nonwoven fabric and a spun lace nonwoven fabric. In its thickness direction, the fibrous assembly layer 3 preferably has a breathability of 5~700 cm$^3$/cm$^2$·sec as measure according to the prescription JIS-L-1096 and a moisture resistance of 0~200 mm as measured according to the prescription JIS-L-1092. Bonding the assembly layer 3 to the upper film layer 2 and to the lower film layer 5 may be carried out using heat- or supersonic-sealing or suitable adhesive agent such as hot melt adhesive agent.

Each of the film strips 5A forming the lower film layer 5 has a thickness of 0.001~0.05 mm, a width $P_1$ of 0.03~1.5 mm. Each pair of adjacent film strips 5A, 5A define therebetween a gap having a width $P_2$ of 0.03~2 mm, preferably of 0.03~1 mm. Similarly to each pair of adjacent plane regions 8 in the upper film layer 2, each pair of adjacent film strips 5A in the lower film layer 5 are also connected to each other via the bridge-like regions extending across the gap left between the adjacent film strips 5A. As will be apparent from FIG. 4, regions 53 corresponding to the openings 9 of the upper film layer 2 projected upon the lower surface of the fibrous assembly layer 2 are partially occupied by the film strips 5A. For example, a particular one 53A of the regions 53 is occupied by the film strip 5A having substantially the same width as the opening lying above this film strip 5A. Another particular region 53B is partially occupied by a side edge portion 54 of the film strip 5A lying immediately beneath the corresponding plane region 8. The film strips 5A may contain suitable colorants such as titanic oxide or barium sulfate.

The menstruation pad serves for its purpose with the upper surface of the core as indicated by two-dot-chain-line being covered with the topsheet 1 constructed as has been described above. With such menstruation pad, menstrual discharge flows into the fibrous assembly layer 3 through the respective openings 9 of the upper film layer 2 and transfers into the core 56 through the gap defined between each pair of adjacent film strips 5A of lower film layer 5.

In the pad after its use, the amount of absorbed menstrual discharge staying beneath the plane regions 8 of the upper film layer 2 and the amount staying beneath the film strips 5A of the lower film layer 5 are substantially inconspicuous to the wearer's eyes by the plane regions 8 and the film strips 5A, respectively. While the amount of menstrual discharge staying in the fibrous assembly layer 3 between each pair of adjacent plane regions 8, 8 otherwise might be seen through the openings 9, such amount of menstrual discharge is effectively inconspicuous to the wearer's eyes by the rising regions 12 so far as these rising regions 12 take their positions leaning inwardly of the openings 9. In this manner, a blot on the pad due to menstrual discharge is not conspicuous even after the pad has been used. The rising regions 12 leaning inwardly of the openings 9 are exemplarily illustrated in FIG. 4 as the rising regions 12D.

The upper surface of such topsheet 1 offers a comfortable velvet touch by the thin and soft rising regions 12 of the upper film layer 2. Using the hydrophilic rising regions 12, it is possible to accelerate transfer of menstrual discharge to the fibrous assembly layer 3 under a capillarity action occurring between each pair of adjacent rising regions 12 along the edges 18 of the plane regions 8 and/or between each pair of rising regions 12 opposed to each other across the opening 9. The component fibers 3A extending upward through the respective openings 9 will act upon menstrual discharge in the same manner as the rising regions 12.

Figure 5:
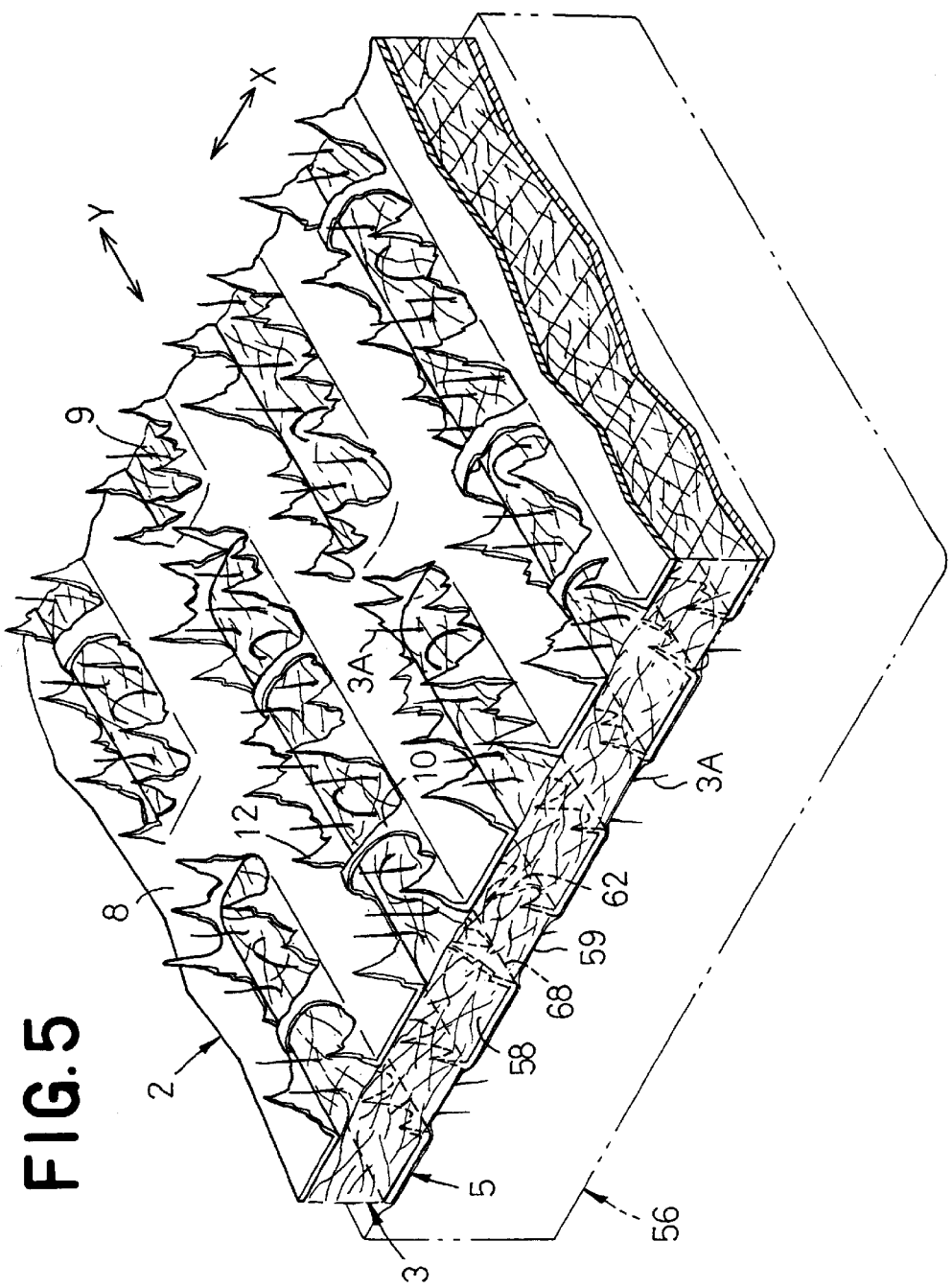
FIG. 5 is a view similar to FIG. 1 but showing another embodiment of the present invention.
Figure 6:
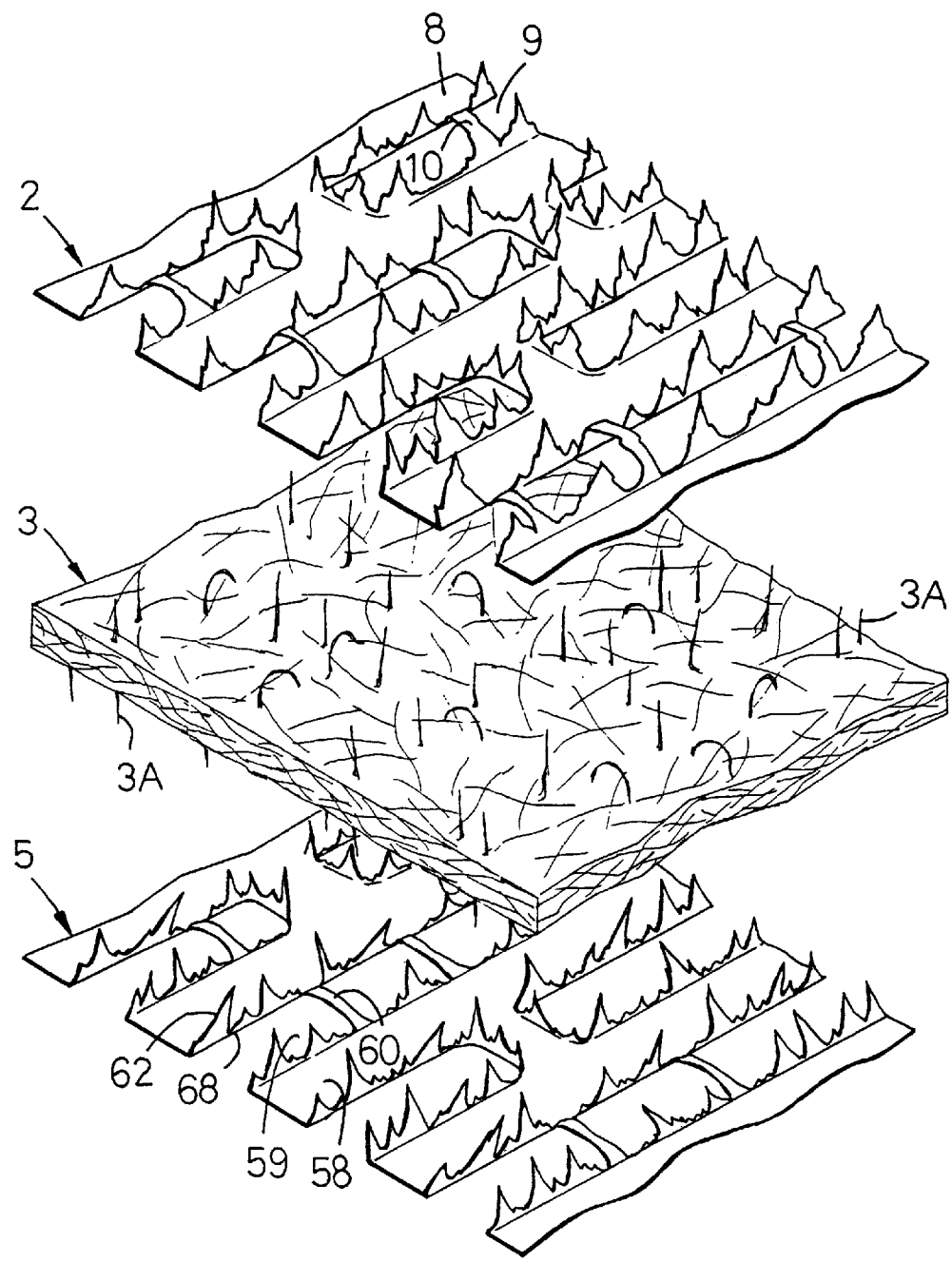
FIG. 6 is an exploded perspective view showing the topsheet of FIG. 5.

FIGS. 5 and 6 are perspective and exploded perspective views similar to FIGS. 1 and 2, respectively, but showing another embodiment of this invention. Referring to FIG. 6, the upper film layer 2, the fibrous assembly layer 3 and the lower film layer 5 are illustrated to be separated one from another in the vertical direction. While the upper film layer 2 and the fibrous assembly layer 3 of these three layers are similar to the corresponding layers 2, 3 in FIG. 2, the lower film layer 5 has a configuration which is not similar to the lower film layer 5 of FIG. 2 but to the upper film layer 2. Specifically, the lower film layer of FIGS. 5 and 6 comprises the plane regions 8, the openings 59, the bridge-like regions 60 and the rising regions 62 extending upward from the edges 68 of the respective plane regions 58. Within the respective openings 9, 59, the component fibers 3A of the fibrous assembly layer 3 extend upward or downward so as to describe straight lines or circular arcs.

The topsheet 1 is formed by placing the upper film layer 2, fibrous assembly layer 3 and lower film layer 5 one upon another and bonding them together. The openings 9 of the upper film layer 2 are aligned with the openings 59 of the lower film layer 5 in the thickness direction of the sheet 1. In other words, the openings 9 respectively have their positions as well as their widths coinciding with the corresponding openings 59 of the lower film layer 5 as viewed in the direction X. However, this is not necessarily true for the relative position between the bridge-like regions 10, 60 associated with the openings 9, 59, respectively. The rising regions 62 of the lower film layer 5 comprise those vertically extending into the fibrous assembly layer 3 from the edges 68 of the respective plane regions 58 and those extending from the edges 68 to lean inwardly of the respective openings 59. The rising regions 62 are readily wettable with menstrual discharge and therefore accelerate the amount of menstrual discharge reaching a level of the rising regions 62 to move downward within the fibrous assembly layer 3 so far as the rising regions 62 are hydrophilic. Even when the rising regions 62 are hydrophobic and not readily wettable with menstrual discharge, the rising regions 62 are effective to prevent the amount of menstrual discharge reaching a level between the arrays of rising regions 62, 62 opposed to each other across the associated opening 59 from spreading laterally beyond the rising regions 62. As a result, such hydrophobic rising regions 62 also accelerate the amount of menstrual discharge reaching a level of the napkin in the vicinity of the openings 59 to move downward. The rising regions 62 extending to lean inwardly of the openings 59 are effective to intercept the amount of menstrual discharge absorbed by the core 56 and lying immediately beneath the respective openings 59 from the wearer's eyes. The bridge-like regions 60 function in the similar manner.

Figure 7:
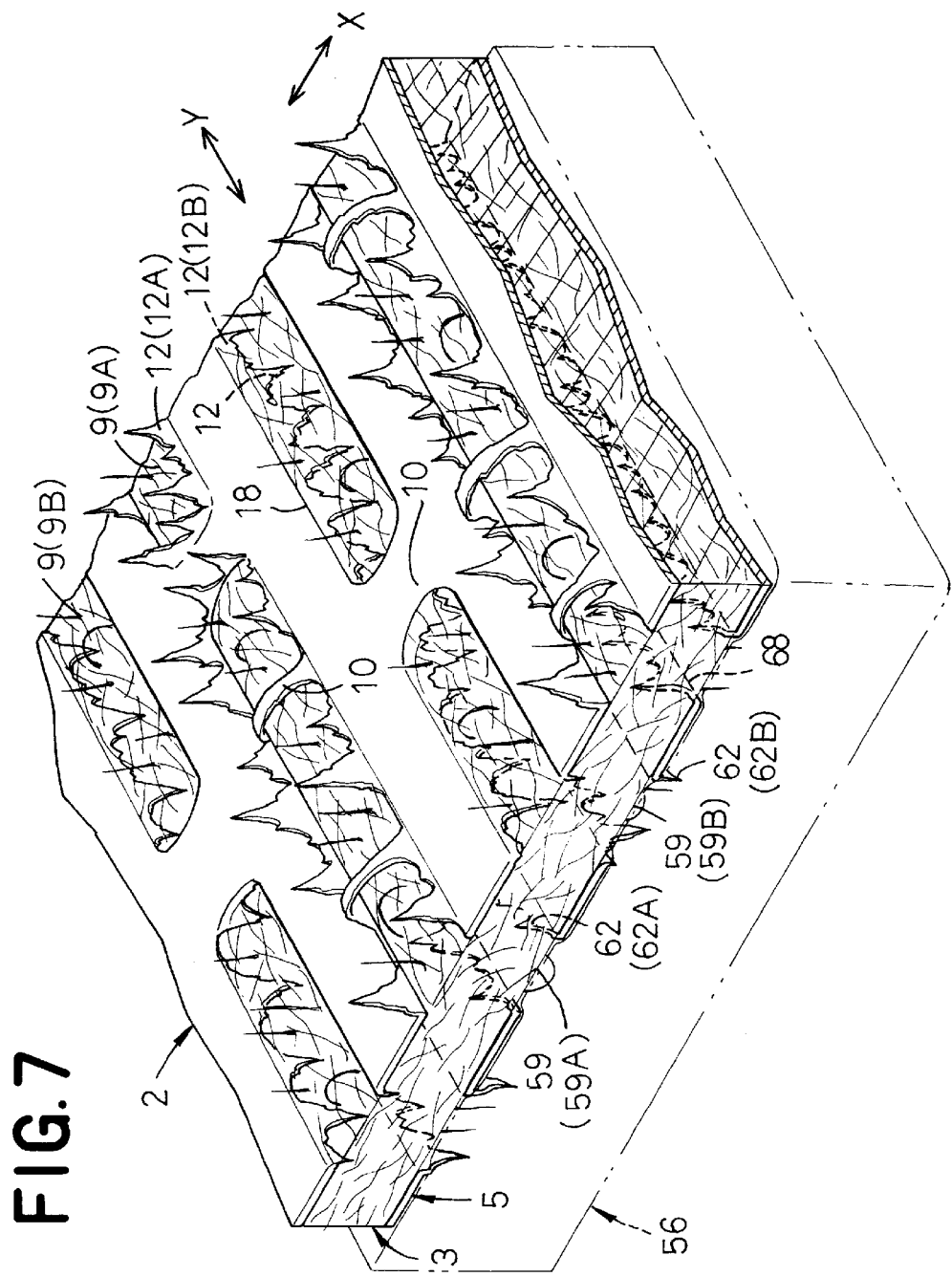
FIG. 7 is a view similar to FIG. 1 but showing still another embodiment of the present invention.
Figure 8:
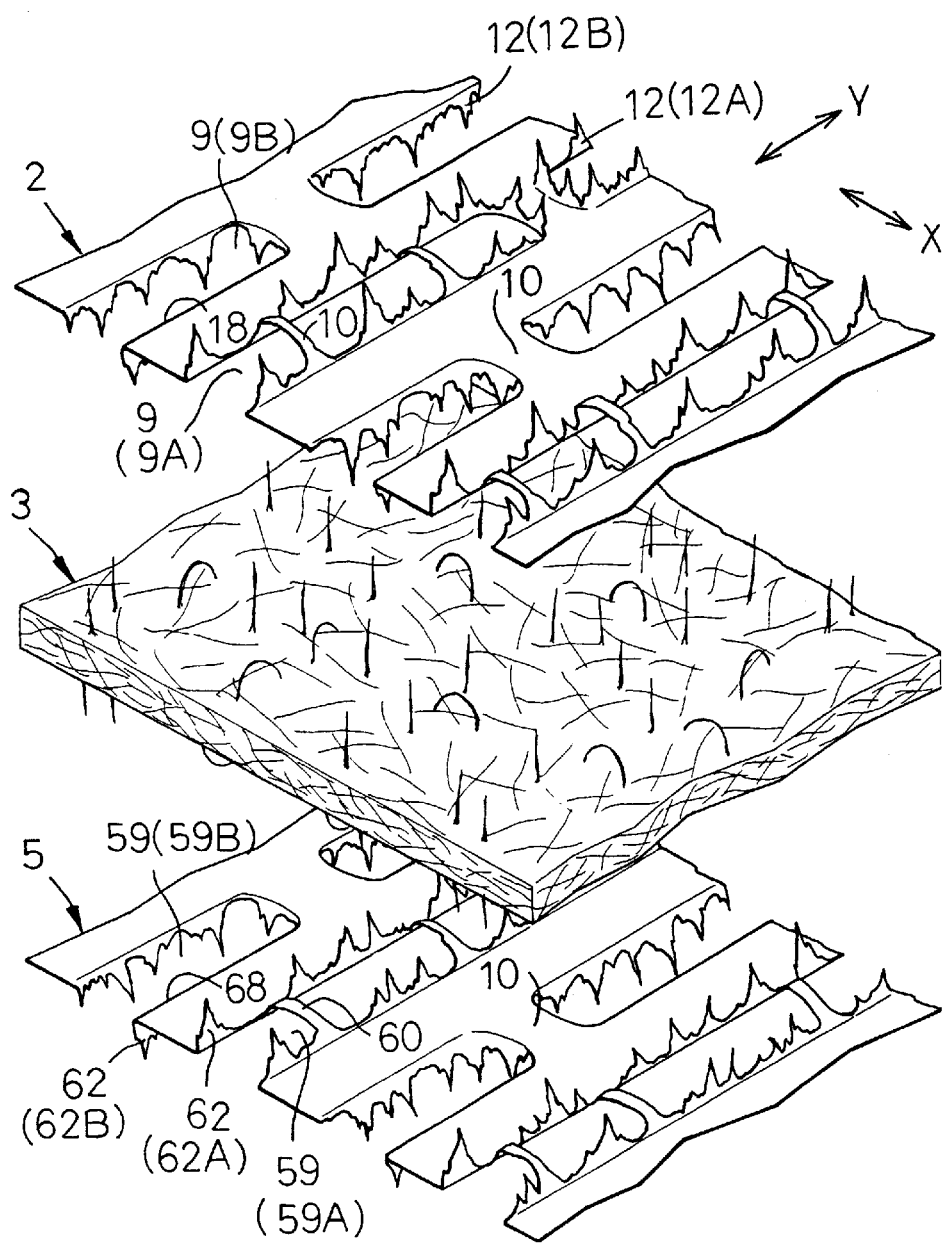
FIG. 8 is an exploded perspective view showing the topsheet of FIG. 7.

FIGS. 7 and 8 are views similar to FIGS. 5 and 6 but showing still another embodiment of this invention. This embodiment is similar to the embodiment of FIGS. 5 and 6 in that the topsheet 1 comprises the upper film layer 2, the fibrous assembly layer 3 and the lower film layer 5 all being similar to those of FIGS. 5 and 6. While the respective openings 9 substantially coincide with the corresponding openings 59 in the widths as well as the positions as measured and viewed in the direction X, this is not necessarily true for the positions as well as the widths of the bridge-like regions 10 and 60 as viewed and measured in the direction Y. The upper and lower film layers 2, 5 are provided along their edges 18, 68 with the rising regions 12, 62, respectively. The rising regions 12, 62 comprise first and third rising regions 12A, 62A both extending upward, and second and fourth rising regions 12B, 62B extending downward. The rising regions 12A, 12B, 62A, 62B comprise those vertically extending up- or downward and those extending to lean inwardly of the openings 9 or 59. In the upper film layer 2, the openings 9A surrounded by the first rising regions 12A and the openings 9B are formed alternately in the direction X. In the direction Y, the openings 9A surrounded by the first rising regions 12A are connected by the bridge-like regions 10 and the openings 9B surrounded by the second rising regions 12B also are connected by the bridge-like regions 10. In the lower film layer 3, the openings 59A surrounded by the third rising regions and the openings 59B surrounded by the fourth rising regions 62B are formed alternately in the direction X. In the direction Y, the openings 59A are connected by the bridge-like regions 60 and the openings 59B also are connected by the bridge-like regions 60.

Though not illustrated, each pair of opposed edges 18, 18 with the opening 9 therebetween are formed along one of these edges with the first rising regions 12A and along the other edge with the second rising regions 12B. Similarly, each pair of opposed edges 68, 68 with the opening 59 are formed along one of these edges with the second rising regions 12B and along the other edge with the fourth rising regions 62B.

With the menstruation pad using the topsheet 1 according to the embodiment shown by FIGS. 7 and 8, the first rising regions 12A of the upper film layer 2 give the topsheet 1 a comfortable touch and accelerate the amount of menstrual discharge reaching the respective openings 9 to move downward. The second rising regions 12B also accelerate the amount of menstrual discharge to move downward since the second rising regions 12B extend into the fibrous assembly layer 3. The third rising regions 62A of the lower film layer 5 accelerate the amount of menstrual reaching the fibrous assembly layer 3 to move downward and the fourth rising regions 62B accelerate the amount of menstrual discharge to move into the core 56 since the rising regions 62B are in contact with the core 56. The component fibers 3A of the fibrous assembly layer 3 will function in the manner similar to the manner in which the fourth rising regions 62B so far as the component fibers 3A are hydrophilic and extend downward from the openings 59. Of the first~fourth rising regions 12A, 12B, 62A, 62B, those extending to lean inwardly of the openings 9 or 59 serve to intercept the amount of menstrual discharge absorbed by the core 56 from the wearer's eyes.

Figure 9:
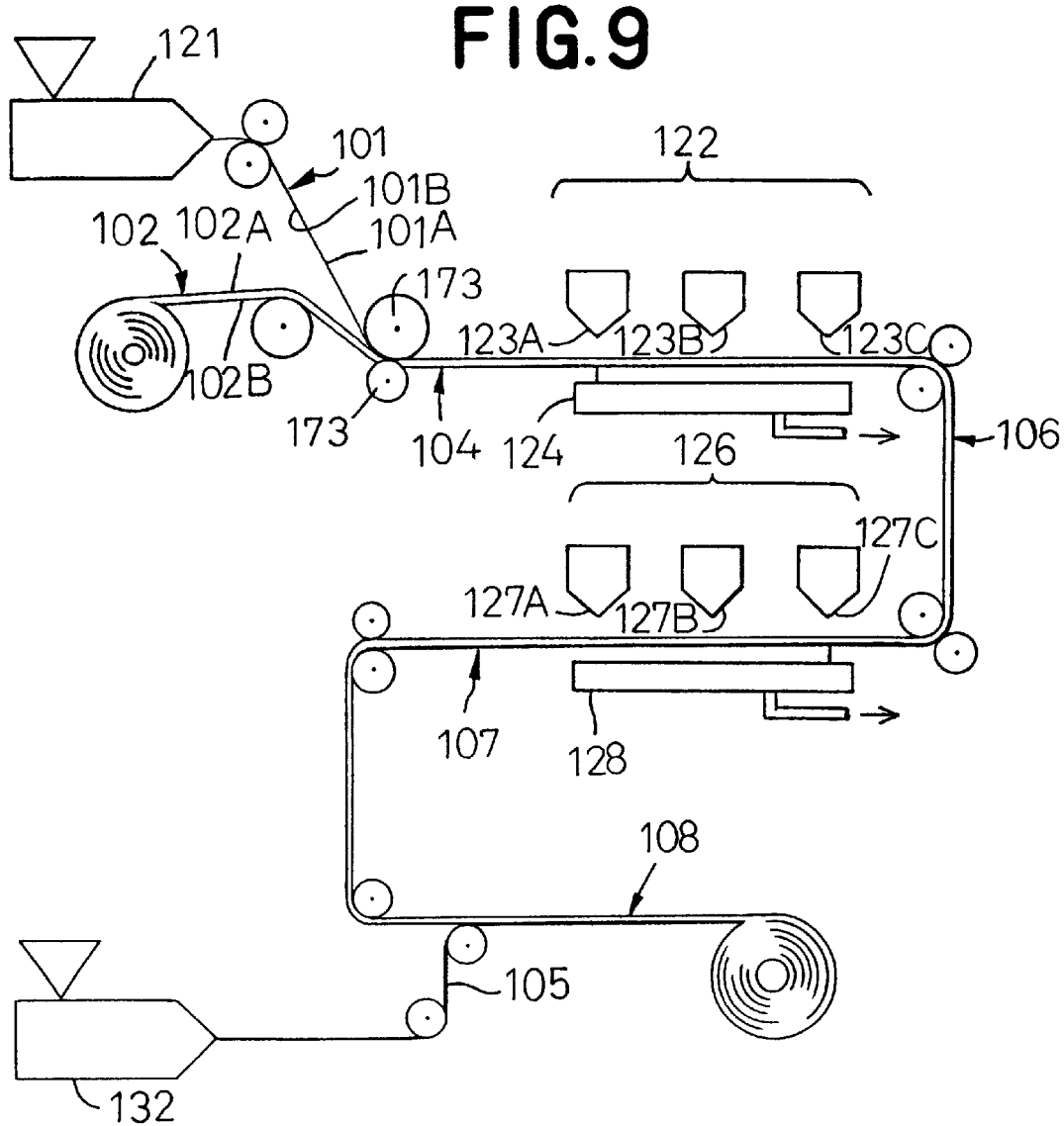
FIG. 9 is a diagram schematically illustrating an embodiment of process for making the topsheet according to the present invention.

FIG. 9 is a diagram schematically illustrating an embodiment of the process according to this invention for making the topsheet of FIGS. 1 and 2. From the left hand as viewed in FIG. 9, first and second webs 101, 102 are continuously fed. The second web 102 comprises a web of fibrous assembly intended to form the fibrous assembly layer 3. The first web 101 intended to form the upper plastic film layer 2 comprises a thermoplastic film fed from an extruder 121 so that the first web 101 in its thermally softened state may be placed upon the second web 102. These first and second webs 101, 102 placed upon each other are fed together between a pair of pressure rolls 173, 173 adapted to bond these two webs 101, 102 to each other and thereby to form first a composite web 104.

The first composite web 104 is then transferred to a first treating zone 122 in which the upper surface 101A of the first web 101 constituting the first composite web 104 is subjected to high pressure columnar water streams ejected from an array 123A of nozzles arranged at a predetermined pitch transversely of the first composite web 104. The first web 101 is ruptured along its locations at which the high pressure columnar water streams directly hit the first composite web 104. Consequently, the first web 101 is formed with a plurality of openings extending in a machine direction (i.e., a direction in which the first composite web 104 is fed) and arranged in parallel one to another transversely of the first composite web 104. In this manner, a second composite web 106 is obtained. Under the effect of the columnar water streams, the component fibers may sometimes partially project downward from the lower surface 102B of the second web 102 so as to describe straight lines or circular arcs. It should be understood that the first treating zone 122 may be provided with, in addition to the array 123A of nozzles, second and third arrays 123B, 123C of nozzles adapted to inject the columnar water streams in order to from said plurality of openings. The nozzle arrays 123A, 123B, 123C are preferably arranged so that the individual nozzles in the respective arrays as viewed transversely of the first composite web 104 may occupy positions substantially aligned one with another and traces of the high pressure water streams may coincide one with another. The first treating zone 122 is provided as its lower part with a suction mechanism 124 adapted to such an excessive amount of water having treated the first composite web 104.

The second composite web 106 is then transferred to a second treating zone 126 provided with a plurality of nozzle arrays 127A, 127B, 127C each comprising a plurality of nozzles arranged transversely of the second composite web 106 and a suction mechanism 128. In the second treating zone 126, high pressure columnar water streams are ejected from the nozzle arrays against the lower surface 102B of the second web 102 making a part of the second composite web 106. The portions of the first web 101 having been shot through by the columnar water streams in the first treating zone 122 are now turned reversely by the columnar water streams, i.e., from the lower surface 101B toward the upper surface 101A of the first web 101 to form a third composite web 107. In this third composite web 107, the component fibers of the second web 102 partially project upward from this second web 102 under the effect of the columnar water streams so as to describe straight lines or circular arcs. It is not essential that the traces formed by the columnar water streams injected from the nozzle arrays 127A, 127B, 127C should coincide with the traces formed by the columnar water streams injected from the nozzle arrays 123A, 123B, 123C in the first treating zone 122. However, the steps of rupturing the first web 101 and reversely turning the portions of the first web 101 having been shot through by the columnar water streams in the first and second treating zones will be easily achieved if the traces formed by the nozzle arrays 123A~123C and the nozzle arrays 127A~127C.

After the third composite web 107 has been subjected to a step of drying, a plurality of film strips 105 formed by a second extruder 132 are fed along the direction in which the third composite web 107 travels and bonded to the rear surface 102B of the second web 102 so that the film strips 105 extend in parallel one to another. The film strips 105 are preferably bonded immediately after they are formed by the second extruder 132, i.e., in their softened state, to the second web 102 under pressure. In the third composite web 107, the film strips 105 are bonded to the rear surface 102B of the second web 102 so that the film strips 105 at least partially lie within the openings formed in the first web. A fourth composite web 108 obtained in this manner is taken up in the form of a roll and eventually cut in an appropriate size to use it as the topsheet 1 of FIG. 1.

In the fourth composite web 108, the openings formed in the first web 101 are destined to define the openings 9 of the topsheet 1 and the portions of the first web 101 shot through by the columnar water streams are destined to define the rising regions 12. The portions of the first web 101 having resisted against the columnar water streams are destined to define the bridge-like regions 10. The film strips 105 are destined to define the lower film layer 5 of the topsheet 1.

Referring to FIG. 9, each of the nozzles in the arrays 123A~123C and 127A~127C preferably has a diameter of 50~150 μm, the nozzles in each array are arranged transversely of the first web 101 preferably at a pitch of 0.2~2 mm, a water pressure is preferably adjusted in a range of 30~200 kg/cm$^2$ and a suction pressure is preferably adjusted in a range of 200~1000 mm $H_2O$. In the first and second treating zones 122, 126, the web to be treated is placed on supporting means such as a mesh screen and conveyed in a desired direction. The first web 101 and the second web 102 as well as the second web 102 and the film strips 105 are fed at a room temperature and respectively bonded together by heat-sealed together between a pair of heated rolls or by use of adhesive agent such as hot melt adhesive agent.

The first web 101, the second web 102 and the film strips 105 may be treated, if desired, to make them hydrophilic at any step of the process for making the topsheet according to this invention. Formation of the openings by the high pressure columnar water streams is facilitated by using the first web 101 uniaxially stretched along the direction in which the first web 101 is fed. The first web 101 and the film strips 105 preferably have a thickness of 0.001~0.05 mm and the second web 102 preferably has a basis weight of 2~50 g/m$^2$.

In the process schematically illustrated by FIG. 9, the first treating zone 122 may be eliminated and the first composite web 104 may be subjected to the high pressure columnar water streams only in the second treating zone 126 to make the topsheet 1. However, such a process may result in the first web 101 having relatively narrow openings and relatively many bridge-like regions since the columnar water streams do not directly act upon the first web 101.

Figure 10:
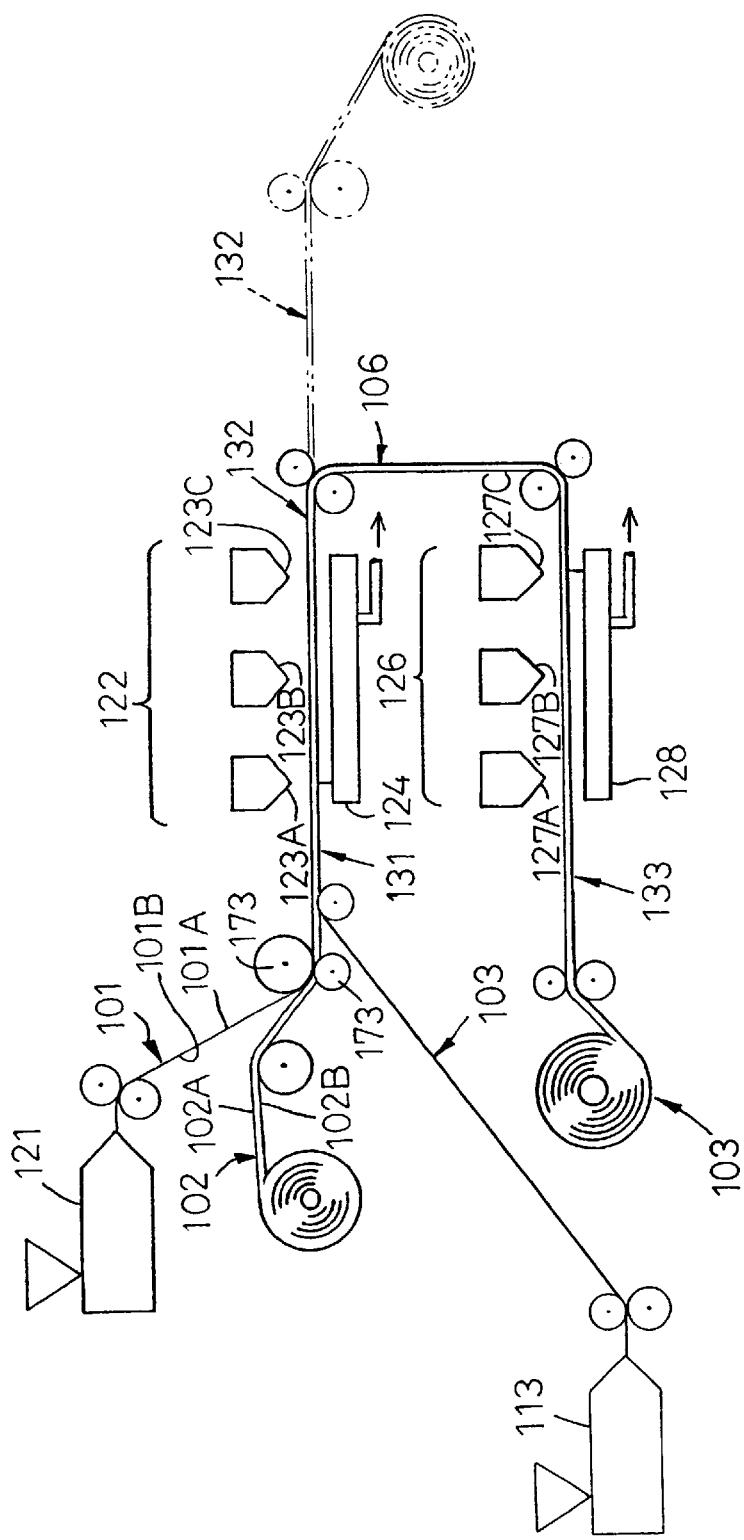
FIG. 10 is a diagram schematically illustrating another embodiment of process for making the topsheet according to the present invention.

FIG. 10 is a diagram similar to FIG. 9 but schematically illustrating another embodiment of the process suitable for making the topsheet 1 of FIGS. 5, 6 as well as the topsheet 1 of FIGS. 7, 8. According to this process, the first web 101 in the form of plastic film in softened state immediately after fed from the first extruder 121 is bonded to the upper surface 102A of the second web 102 in the form of fibrous assembly, on one hand, and the third web 103 in the form of plastic film in softened state immediately after fed from a third extruder 113 is bonded to the lower surface 102B of the second web 102, on the other hand. The third web 103 is destined to define the lower plastic film layer 5 of the topsheet 1. In this manner, a fifth composite web 131 is obtained. The fifth composite web 131 has its first web 101 treated by the high pressure columnar water streams ejected from the nozzle arrays 123A, 123B, 123C in the first treating zone 122. As a result, a sixth composite web 132 is obtained, in which the first and web 101 and the third web 103 both made of a plastic film are formed with a plurality of plane regions and a plurality of openings both extending in the machine direction. The sixth composite web 132 may be taken up in the form of a roll as indicated by imaginary lines. The sixth composite web 132 taken up in this manner has, in addition to the plane regions and the openings, the rising regions extending from the edges of the plane regions in the direction of the water streams and the bridge-like regions extending across the respective openings all formed in the first and third webs 101, 103. Such sixth composite web 132 is useful as the topsheet 1 of FIGS. 5 and 6, in which the first web 101, the openings, the rising regions and the bridge-like regions formed in the first web 101 are destined to define the lower film layer 5, the openings 59 and the rising regions 62 of the topsheet 1, respectively. The third web 103, the openings, the rising regions and the bridge-like regions formed in the third web 103 are destined to define the upper film layer 2, the openings 9, the rising regions 12 and the bridge-like regions 10 formed in said third web 103. The component fibers of the second web 102 may project up- or downward from the openings 59. The third web 103 preferably is made of film having a thickness of 0.001~0.05 mm.

It is also possible to convey the sixth composite web 132 to the second treating zone 126 instead of taking up in the manner as has been described above. In this case, the sixth composite web 132 has its third web 103 is subjected to the high pressure columnar water streams ejected from the nozzle arrays 127A, 127B, 127C in the second treating zone 126 to obtain a seventh composite web 133. A distance between each pair of adjacent nozzles in the respective nozzle arrays 127A, 127B, 127C each arranged transversely of the sixth composite web 132 is preferably dimensioned to be twofold or integral-fold larger than the corresponding distance in the first treating zone 122 and some of the nozzles in the second treating zone 126 are preferably positioned to substantially coincide with some of the nozzles in the first treating zone 122. By arranging the nozzles in the second treating zone 126, some of the openings in the sixth composite web 132 arranged transversely of this composite web 132 will be treated again in the second treating zone 126. In the vicinity of these retreated openings, the rising regions of the first and third webs 101, 103 are reversely turned by the columnar water streams to rise from the third web 103 toward the first web 101. At the same time, the component fibers of the second web 102 may project upward from the openings. In the openings not treated in the second treating zone 126, the rising regions remain to be oriented as in the sixth composite web 132. Of the seventh composite web 133, the first web 101 may be used as the upper film layer 2 of the topsheet 1 or the third web 103 may be used as the upper film layer 2.

It should be understood that the second treating zone 126 may include, in addition to the nozzle arrays 127A, 127B, 127C adapted to reverse the orientation of the rising regions, nozzle arrays adapted to form the third web 103 and/or the first web 101 with new openings, new rising regions extending along these openings and new bridge-like regions extending across these respective openings.

The liquid-pervious topsheet according to this invention enables the core soiled with body fluids to be inconspicuous to a wearer eyes because the surface of the core is directly or indirectly covered with the plastic film over a large area thereof. In this novel topsheet, the fibrous assembly has its upper and lower surface provided with the plastic film bonded thereto wherein the upper film is formed with a plurality of rising regions extending upward to give a comfortable velvet touch. When both the upper film and the lower film are formed with a plurality of rising regions, in addition to the comfortable velvet touch, these rising regions accelerate body fluids to move downward from the upper surface of the topsheet toward the lower surface thereof and from the topsheet toward the core.

What is claimed is:

1. A liquid-pervious composite plastic topsheet for a disposable absorbent article which comprises:

a first plastic film layer defining an upper surface of said composite plastic topsheet, a second plastic film layer defining a lower surface of said composite plastic topsheet; and a fibrous layer disposed between and joined to the first and second plastic film layers, said first plastic film layer having an upper surface, a lower surface, a thickness of from about 0.001 to about 0.05 mm, a plurality of substantially flat portions having widths of from about 0.03 to about 1 mm and extending in parallel to one another in a first direction, and a plurality of intermittent apertures extending in said first direction between said substantially flat portions so as to form a plurality of aperture rows extending in parallel one to another in said first direction, pairs of said flat portions having said aperture rows therebetween being interconnected by a plurality of bridge portions that extend therebetween and across said aperture rows, said bridge portions extending across the respective aperture rows are formed intermittently in a second direction orthogonal to the first direction, providing two types of bridge portions, those which extend upward or downward from the upper surface of the flat portions to the upper surface of the respective adjacent flat portions so as to describe arcs and those which are flush with the flat portion, said intermittent apertures being defined by edges of said substantially flat portions which extend in said first direction and edges of said bridges portions which extend in said second direction, said substantially flat portions being formed at least along said edges thereof which extend in said first direction with a plurality of first substantially pointed tooth-shaped portions which extend upward from upper surfaces of said substantially flat portions, said second plastic film layer comprising a plurality of discrete elongate strip portions that extend parallel to one another in the first direction and are spaced apart in said second direction, individual ones of said plurality of discrete elongate strip portions being aligned and configured to lie beneath at least a portion of one of each of the aperture rows of the first plastic film layer.

2. The topsheet according to claim 1, wherein said fibrous layer contains at least 5 wt. % hydrophilic fibers.

3. The topsheet according to claim 1, wherein said substantial flat portions of the first plastic film layer are further formed along said edges thereof which extend in said first direction with a plurality of second substantially pointed tooth-shaped portions which extend downward from lower surfaces of said substantially flat portions.

4. The topsheet according to claim 3, wherein said second substantially pointed tooth-shaped portions extend into fiber interstices of said fibrous layer.

5. The topsheet according to claim 1, wherein said second substantially pointed tooth-shaped portions of the substantially flat portions extend so as to lean toward adjacent ones of the substantially flat portions.

6. The topsheet according to claim 1, wherein said fibrous layer comprises a nonwoven fabric.

* * * * *